United States Patent [19]
DiCaprio

[11] Patent Number: 6,036,697
[45] Date of Patent: Mar. 14, 2000

[54] BALLOON CATHETER WITH BALLOON INFLATION AT DISTAL END OF BALLOON

[75] Inventor: Fernando DiCaprio, Mendota Heights, Minn.

[73] Assignee: Scimed Life Systems, Inc., Maple Grove, Minn.

[21] Appl. No.: 09/112,387

[22] Filed: Jul. 9, 1998

[51] Int. Cl.$^7$ ........................................ A61F 11/00
[52] U.S. Cl. .............................. 606/108; 606/192; 604/96
[58] Field of Search ................... 606/108, 1, 10, 606/191–198; 623/1, 12; 604/96

[56] References Cited

U.S. PATENT DOCUMENTS

| | | |
|---|---|---|
| 4,093,484 | 6/1978 | Harrison et al. . |
| 4,154,244 | 5/1979 | Becker et al. . |
| 4,250,872 | 2/1981 | Tamari ........................................ 128/1 |
| 4,367,747 | 1/1983 | Witzel . |
| 4,411,055 | 10/1983 | Simpson et al. . |
| 4,413,989 | 11/1983 | Schjeldahl et al. . |
| 4,456,000 | 6/1984 | Schjeldahl et al. . |
| 4,587,975 | 5/1986 | Salo et al. . |
| 4,637,396 | 1/1987 | Cook . |
| 4,692,200 | 9/1987 | Powell ........................................ 606/192 |
| 4,735,665 | 4/1988 | Miahuchi et al. . |
| 4,740,207 | 4/1988 | Kreamer . |
| 4,932,956 | 6/1990 | Reddy et al. ........................... 606/192 |
| 4,950,227 | 8/1990 | Savin et al. . |
| 5,007,926 | 4/1991 | Derbyshire . |
| 5,015,230 | 5/1991 | Martin et al. . |
| 5,163,906 | 11/1992 | Ahmadi . |
| 5,172,222 | 12/1992 | Plantier et al. . |
| 5,176,968 | 1/1993 | Burns et al. . |
| 5,207,700 | 5/1993 | Euteneuer . |
| 5,219,335 | 6/1993 | Willard et al. . |
| 5,226,880 | 7/1993 | Martin . |
| 5,226,889 | 7/1993 | Sheiban . |
| 5,250,069 | 10/1993 | Nobuyoshi et al. . |
| 5,290,295 | 3/1994 | Querals et al. . |
| 5,290,306 | 3/1994 | Trotta et al. . |
| 5,304,197 | 4/1994 | Pinchuk et al. . |
| 5,334,146 | 8/1994 | Ozasa .......................................... 604/96 |
| 5,334,148 | 8/1994 | Martin . |
| 5,338,295 | 8/1994 | Cornelius et al. . |
| 5,344,400 | 9/1994 | Kaneko et al. . |
| 5,409,495 | 4/1995 | Osborn .................................... 606/108 |
| 5,445,646 | 8/1995 | Euteneuer et al. . |
| 5,458,615 | 10/1995 | Klemm et al. . |
| 5,507,768 | 4/1996 | Lau et al. . |
| 5,545,138 | 8/1996 | Frugoso et al. ........................... 606/192 |
| 5,707,354 | 1/1998 | Salmon et al. . |
| 5,738,667 | 4/1998 | Solar ........................................ 604/280 |
| B1 4,733,664 | 1/1994 | Palmaz . |
| B1 5,209,728 | 4/1998 | Kraus et al. . |

FOREIGN PATENT DOCUMENTS 0 707 837 A1   4/1996   European Pat. Off. .

*Primary Examiner*—Michael Buiz
*Assistant Examiner*—Lien Ngo
*Attorney, Agent, or Firm*—Vidas, Arrett & Steinkraus

[57] ABSTRACT

A balloon catheter is provided having an expandable distal portion, said expandable portion having a proximal end, a distal end and distal expansion means, said expandable portion being adapted for expansion at its distal end, from its distal end to its proximal end. A stent delivery system is provided to facilitate introduction and placement of a stent, and includes a catheter having an expandable distal portion constructed and arranged for expanding the outer diameter of the catheter from a contracted state to an expanded state, said distal portion further comprising a balloon, and a stent positioned around the distal portion of the catheter around the balloon, said stent having a proximal end and a distal end and further having a contracted condition, said stent being sized in the contracted condition to closely surround the balloon in the contracted state, and being adapted to expand to an expanded condition from its distal end to its proximal end in response to expansion of the balloon member from its distal end.

28 Claims, 8 Drawing Sheets

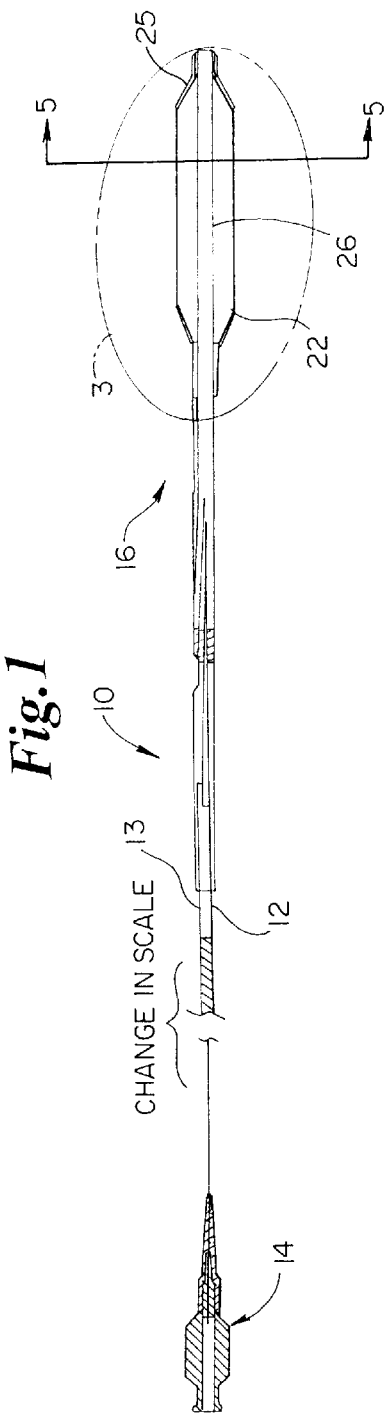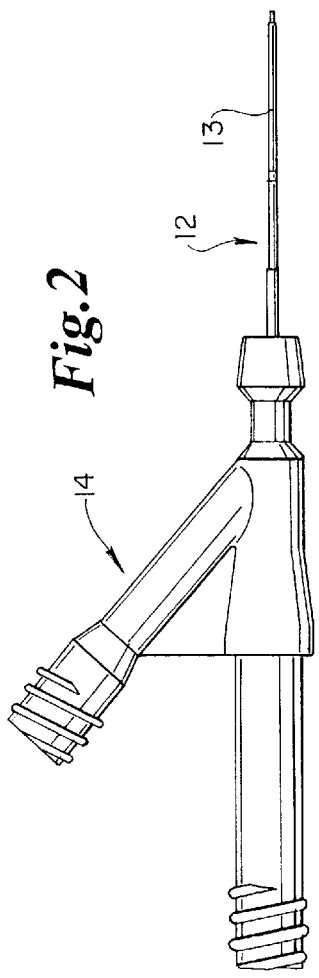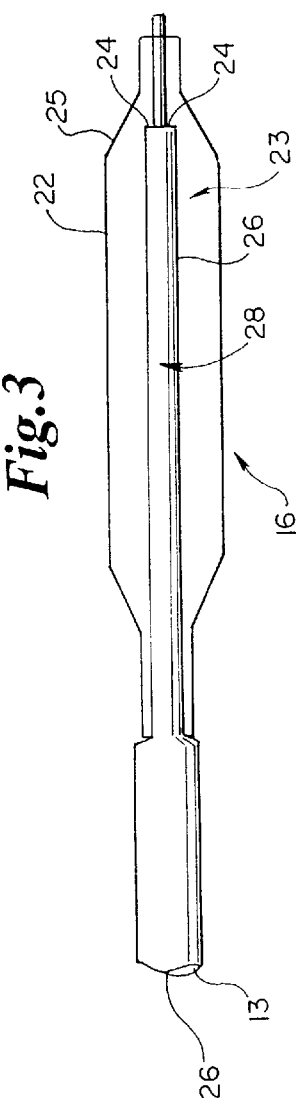

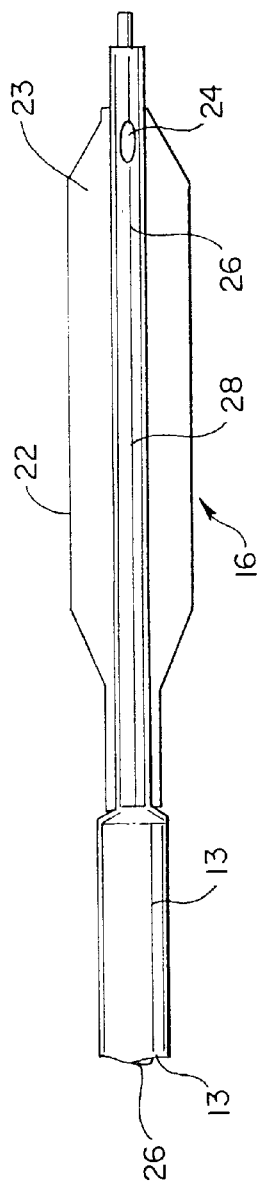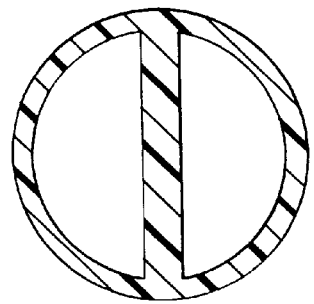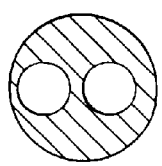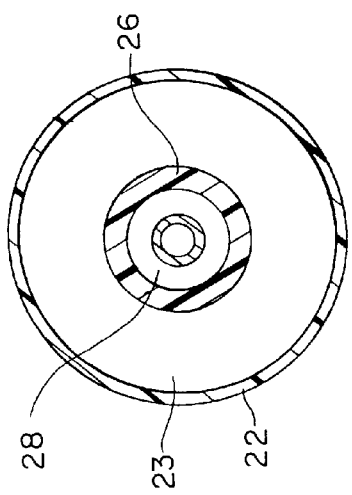

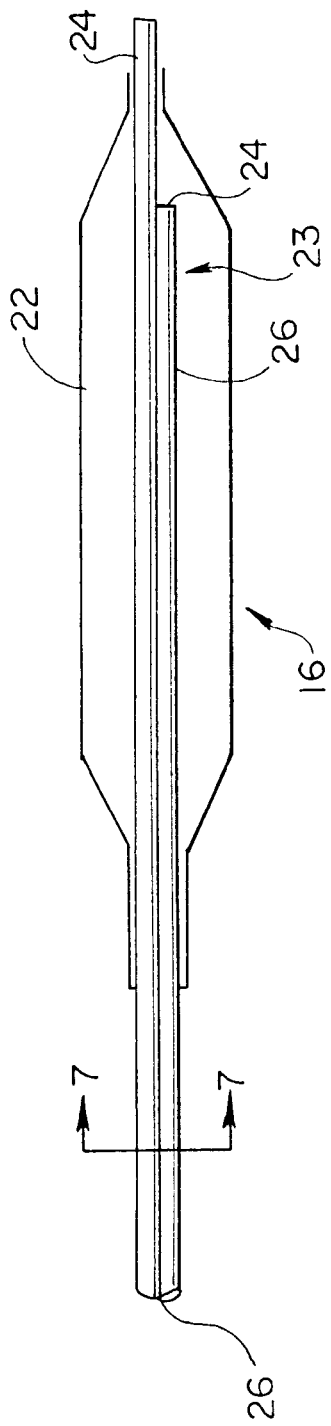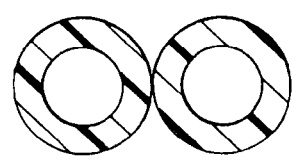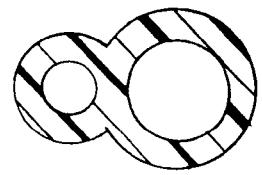

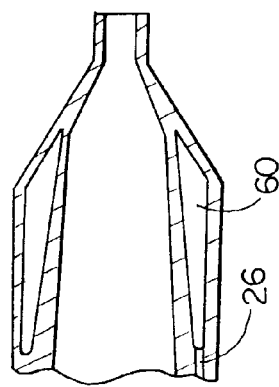
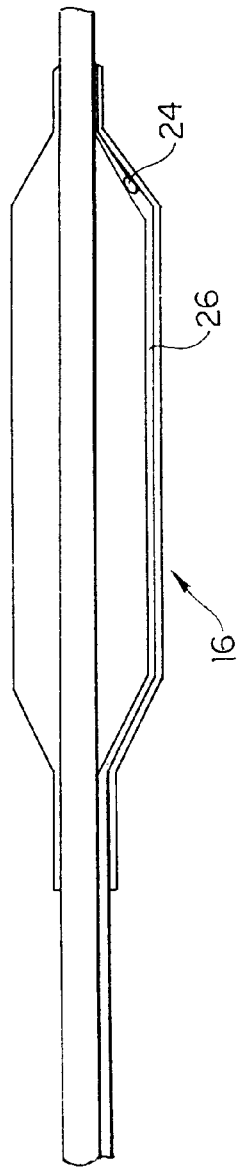
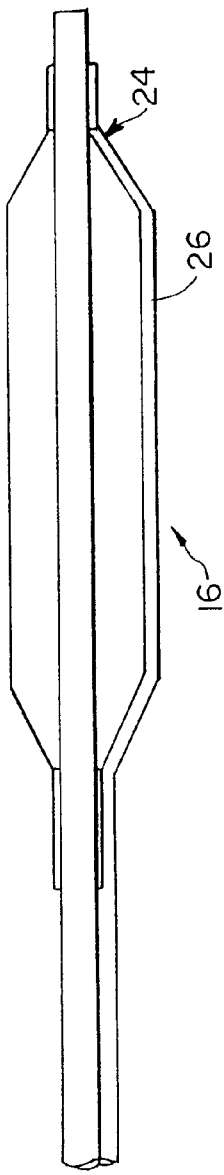

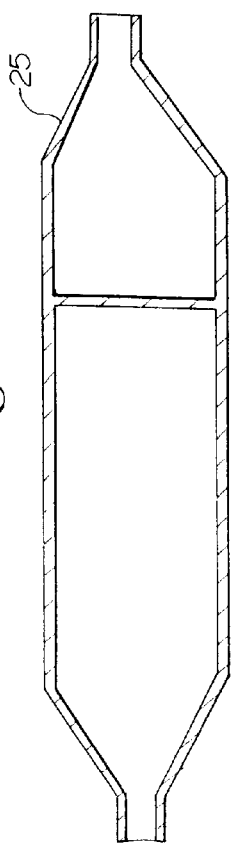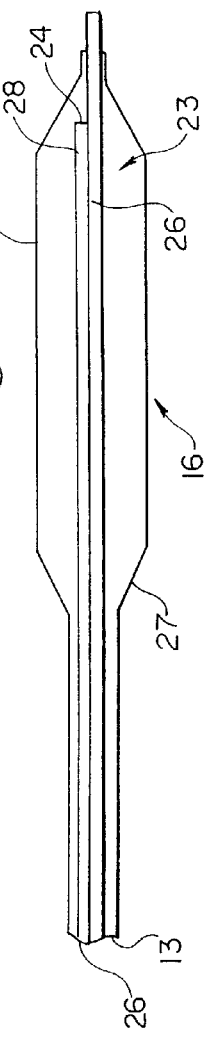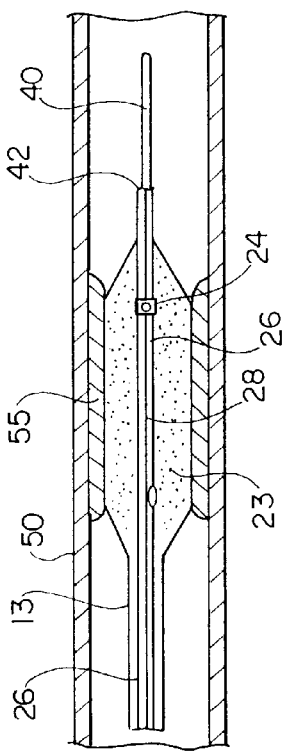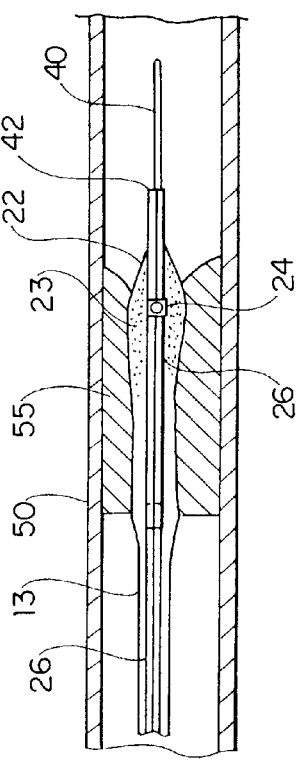

BALLOON CATHETER WITH BALLOON INFLATION AT DISTAL END OF BALLOON

BACKGROUND OF THE INVENTION

The present invention relates generally to catheters having an expandable balloon and to premounted balloon expandable stent balloon catheters, and specifically to a balloon catheter with expansion means at the distal end of the balloon. The present invention is particularly directed to improved arrangements of the balloon member of a balloon catheter which provides inflation of the balloon from its distal end to its proximal end, and to improved arrangements of a stent delivery catheter which provides expansion of the stent from its distal end to its proximal end.

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries may also become blocked due to formation of thrombus. Percutaneous transluminal angioplasty (PTA) is also a known treatment of body lumens.

The most widely used form of percutaneous angioplasty makes use of a dilatation balloon catheter. In typical PTCA or PTA procedures, the cardiovascular system of a patient is accessed with an introducer, usually via the femoral artery or the radial artery. All other devices including a guiding catheter are percutaneously introduced into the cardiovascular system of a patient through the introducer and advanced through a vessel until the distal end thereof is at a desired location in the vasculature. A guide wire and a dilatation catheter having a balloon on the distal end thereof are introduced through the guiding catheter with the guide wire sliding through the dilatation catheter. The guide wire is first advanced out of the guiding catheter into the patient's coronary vasculature and the dilatation catheter is advanced over the previously advanced guide wire until the dilatation balloon is properly positioned across the lesion. Once in position across the lesion, the flexible, expandable, preformed balloon is inflated to a predetermined size with a fluid at relatively high pressures, such as greater than about four atmospheres, to radially compress or fracture the atherosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

Following angioplasty procedures of the kind described above, there is a possibility of restenosis of the artery. Restenosis may necessitate either another angioplasty procedure, a surgical by-pass operation, or some method of repairing or strengthening the area. To reduce the likelihood of restenosis and strengthen the area, a physician can implant an intravascular prosthesis for maintaining vascular patency, called a stent, inside the artery at the lesion. In general, stents are prosthetic devices which can be positioned within a body cavity, for example, a blood vessel of the body of a living human or in some other difficulty accessible place. A stent generally has a variable diameter, which may be increased or decreased. Stents are particularly useful for permanently widening a vessel which is in a narrowed state, or for internally supporting a vessel damaged by an aneurysm.

Such stents are typically introduced into the body cavity by use of a catheter. The catheter is usually of the balloon catheter type in which the balloon is utilized to expand the stent, which is positioned over the balloon, to place it in a selected location in the body cavity. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. No. 4,740,207 to Kreamer and U.S. Pat. No. 5,007,926 to Derbyshire.

One important characteristic of a dilatation balloon catheter is the manner in which the balloon inflates. Prior art balloon catheters are constructed such that the inflation fluid enters the balloon at the proximal end. The balloon catheter of the present invention provides a construction wherein the fluid enters the balloon at the distal end thereof, resulting in expansion of the balloon from its distal end to its proximal end. When used with balloon expandable stents, the balloon and balloon catheter of the present invention allows for the stents to dilate distally first and then expand proximally. Current designs have stents either "dumbbell", i.e. open at both ends, or open proximally first. The distal inflation provided by the present invention prevents the release or dislodgment of thrombus or plaque downstream. In addition, distal to proximal inflation serves to minimize vessel wall trauma resulting from stent "dumbbelling".

SUMMARY OF THE INVENTION

It is a general object of the present invention to provide an improved medical balloon and a medical device incorporating a balloon. This invention concerns medical devices such as balloon catheters and apparatus suitable for delivery of stents to body cavities. The present invention is particularly directed to improved balloon catheters and to improved arrangements for balloon inflation, the improvement comprising distal balloon inflation means providing inflation from the distal end to the proximal end. Another object of the present invention is to provide an improved means and method for expanding a medical balloon (and a stent carried thereon) from the distal end to the proximal end.

Accordingly, the present invention provides a catheter having an expandable distal portion constructed and arranged for expanding the outer diameter of the catheter from a contracted state to an expanded state. The distal portion of the catheter comprises a balloon which is folded or otherwise collapsed, and is expandable to an expanded condition by introduction of an inflation fluid. The balloon catheter may comprise an outer lumen with a balloon member attached to and/or extending distally therefrom, and an inner lumen extending the length of the outer lumen and distally therefrom through the interior portion of the balloon member. At its proximal end, the balloon member is positioned around the inner lumen and abuts the distal end of the outer lumen. The distal end of the outer lumen may be a second (softer, more compliant) material bonded to the proximal end. The catheter is associated with a source of inflation fluid. Alternatively, where the balloon member is attached to the outer lumen, the outer lumen of the catheter may extend distally into the interior of the balloon member.

At the distal portion of the balloon member, the catheter comprises a distal inflation port through which inflation fluid is introduced into the distal portion of the balloon. A separate inflation lumen may also be provided which extends through the catheter and comprises the distal inflation port. Where the catheter and balloon have a unitary construction, a separate inflation lumen is provided.

It is also an object of the present invention to provide an improved means and method for delivery of a stent via a catheter having an expandable balloon which expands from the distal to the proximal end. Accordingly, the present invention also provides a catheter balloon having an expandable distal portion constructed and arranged for expanding the outer diameter of the stent from its distal end to its proximal end.

The present invention also provides a stent delivery system including a catheter balloon having an expandable distal portion constructed and arranged for expanding the outer diameter of the stent from a contracted state to an expanded state from its distal end first. A stent is positioned around the distal portion of the catheter and over the balloon. The balloon catheter of the present invention, when used with balloon expandable stents, allows for the stents to dilate distally first and then expand proximally. Prior art catheter balloons, however, cause the stents to either open proximally first, or "dumbbell", i.e. expand from both ends to the center when the balloon inflates.

Important advantages are provided by the distal to proximal inflation provided according to the present invention. Distal inflation prevents the release or dislodgment of thrombus or plaque downstream. In addition, distal to proximal inflation serves to minimize vessel wall trauma resulting from stent "dumbbelling".

BRIEF DESCRIPTION OF THE FIGURES

FIG. 1 is a perspective view of a balloon catheter according to the present invention, the catheter being of the monorail or single operator exchange (SOE) type, with the distal portion of the catheter shown in larger scale than the proximal portions and showing a balloon inflation means located at the distal end thereof;

FIG. 2 is a perspective view of the proximal section of an alternative catheter of the over the wire type, with which the balloon of the present invention may be utilized;

FIG. 3 is an enlarged view in longitudinal cross-section of the distal portion of the catheter of FIG. 1 (indicated by dashed circle 3 at FIG. 1);

FIG. 4 is a longitudinal cross section of an alternative embodiment of the distal portion of the catheter of the present invention;

FIGS. 5A–5C are alternative cross sectional views along line 5—5 at FIG. 2;

FIG. 6 is a longitudinal cross section of an alternative embodiment of the distal portion of the catheter of the present invention;

FIGS. 7A–7B are cross sectional views of alternative embodiments along line 7—7 at FIG. 6;

FIG. 8A is a longitudinal cross section of an alternative embodiment of the distal portion of the catheter of the present invention, and FIG. 8B is a fragmentary cross section of an alternative embodiment of the distal portion of the balloon thereof;

FIG. 9 is a longitudinal cross section of an alternative embodiment of the distal portion of the catheter of the present invention;

FIG. 10 is a longitudinal cross section of an alternative embodiment of a balloon according to the present invention.

FIG. 11 is a longitudinal cross section of a further alternative embodiment of the distal portion of the catheter of the present invention;

FIGS. 12–16 are longitudinal section views of expansion of the balloon member of the catheter of the present invention;

DETAILED DESCRIPTION OF THE INVENTION

Figure 14:
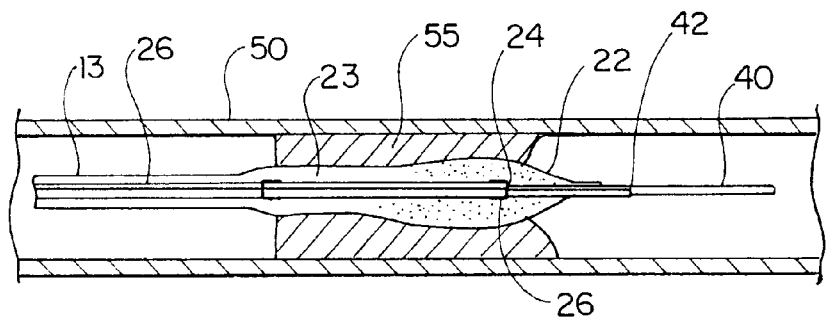

Referring to FIGS. 1–5, a medical device comprising a balloon catheter with a balloon member according to the present invention is generally indicated at 10. FIG. 1 is a longitudinal section view of a balloon catheter with a balloon according to the present invention, wherein the balloon inflation means is located at the distal portion of the balloon thereof.

As shown at FIG. 1, catheter 12 has a shaft 13, a proximal portion 14 and a distal portion, indicated generally at 16. The catheter shown at FIG. 1 is a monorail or single operator exchange (SOE) type catheter. A perspective view of an alternative embodiment of proximal portion 14 is shown at FIG. 2, specifically an over the wire type catheter device. It is understood that any suitable catheter known in the art including but not limited to monorail, SOE or over the wire type catheters may be used according to the present invention.

Distal portion 16 is shown at FIG. 1 in longitudinal section view which is enlarged relative to the view of the proximal portion of said catheter. Distal portion 16 is fixed to catheter 12 by standard means known in the art. For instance, distal portion 16 may be bonded, by adhesive or any kind of bonding technologies including but not limited to heat bonding, to the catheter in an integral manner. Alternatively, distal portion 16 may be may be of unitary construction, i.e. made one-piece with the catheter as is known in the art. Distal end portion 16 comprises balloon 22, which is constructed and arranged for expansion from a contracted state to an expanded state.

Balloon 22 may be of any length. For instance, balloon 22 may be about 15 mm long. This length, however, is for illustrative purposes only and is not meant to be limiting. Balloon 22 is shown in a partially inflated state in FIGS. 1, 3, 6, 8–11 and 16. Balloon 22 may be contracted, folded or otherwise collapsed.

Balloon 22 may be made of a material which resiliently deforms under radial pressure. Examples of suitable materials are generally known in the art and include non-compliant, semi-compliant and compliant materials such as polyethylene (PE), nylon, polyamide, polyether block amides (PEBAX), polyethylene terephthalate (PET), silicone, POC, polypropylene, polyether block PBT and the like. In addition, balloon 22 may be formed of multiple layers of these materials and/or coextruded. Further, balloon 22 may comprise fiber reinforcements, such as are disclosed in U.S. patent application Ser. No. 08/817,165 incorporated herein by reference. Balloon 22 may be provided with a distal end 25 made of a second softer more compliant material bonded to the proximal end 27.

The balloon may be integrally molded with the catheter (as shown at FIG. 10) or bonded to the catheter shaft (as shown at FIGS. 4, 6, 8 and 9). Where a separate balloon is provided, it is bondable to the catheter by any suitable adhesive, for example, epoxy adhesives, urethane adhesives, cyanoacrylates, and other adhesives suitable for bonding nylon or the like, as well as by hot melt bonding, ultrasonic welding, heat fusion or the like. Alternatively such a balloon may be attached to the catheter by mechanical means such as swage locks, crimp fittings, threads and the like.

Where the catheter is separate from the balloon (and bonded thereto), the catheter may be made of high density or low density polyethylene, nylons, Pebax, Grilamid, Vestamid, Cristamid, or combinations thereof. The catheter shaft could also be made of a metal, such as stainless steel (ss hypotube, for example), Nitinol or the like, optionally with a lubricious exterior added thereto, such as a hydrophilic coating (for example, as described in U.S. Pat. No. 5,693,034, incorporated herein by reference) or silicone coating.

Figure 15:
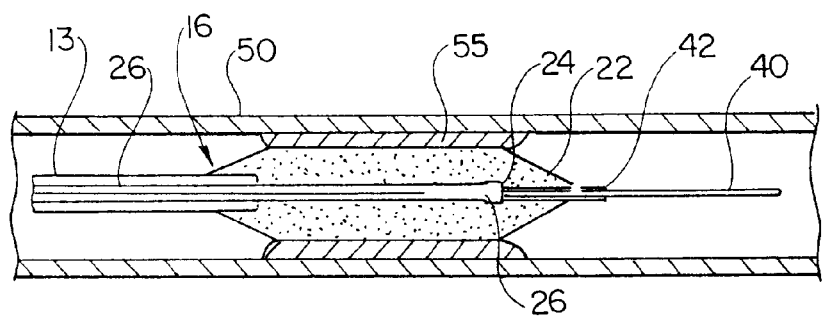

In use, balloon 22 has a larger diameter which is obtained when the balloon 22 is expanded. FIG. 15 shows distal end portion 16 in an even more enlarged longitudinal cross-sectional view, in use. Catheter balloon 22 is inflated by fluid (gas or liquid) from distal inflation port 24 (shown at FIGS. 3 and 4) extending from inflation lumen 26 contained in the catheter shaft 13 and opening into the distal portion of balloon 22.

As shown at FIG. 1, the catheter may be associated with a source of fluid (gas or liquid) external to the catheter and associated therewith, whereby the fluid is delivered to the balloon or expandable member by inflation lumen 26 located in the catheter shaft 13 and associated with distal portion of balloon 22. FIG. 5A–5C are cross sections of balloon 22 along line 5—5 of FIG. 1, showing interior 23 of balloon 22, inflation lumen 26, the interior 28 of inflation lumen 26, and optional guide wire lumen 42. As shown at FIGS. 3, 4 and 5A, balloon 22, inflation lumen 26 and guide wire lumen 42 have a coaxial configuration. FIGS. 5B and 5C show a dual-lumen configuration which may be formed in a single extrusion process. Lumens 26 and 42 as shown at FIG. 5B are of a circular cross section. Alternatively, as shown at FIG. 5C lumens 26 and 42 may be of a semicircular cross section.

Referring now to FIG. 6, an alternative embodiment of the catheter having a dual-lumen configuration is shown. FIGS. 7A–7B are cross sectional views of alternative embodiments taken along line 7—7 of FIG. 6. As exemplified by FIG. 7A, the dual lumen configuration may be formed in a single extrusion process. Alternatively, two individual tubes may be joined together by an adhesive joint or a thermal process. FIG. 7B shows two individual tubes. A single extrusion, dual lumen tubing is the preferred configuration.

Balloon 22 may be distally inflated by other means, such as from fluid communication at its distal end from a passageway or passageways formed between the outside of the catheter shaft and the membrane forming the balloon, depending on the design of the catheter. An example of a balloon having a passageway formed between the outside of the catheter shaft and the membrane forming the balloon is shown at FIG. 8A. Such a passageway could lead from the catheter shaft directly to the interior of the balloon via a conduit ending at the distal portion of the balloon, as shown at FIG. 6. Alternatively, the passageway could lead to the exterior of the balloon to an exterior distal inflation port 24', as shown in FIG. 9.

In addition, the passageway could lead not only to the interior of the balloon, but also to a distal inflation compartment located at the distal end of the balloon. A distal inflation compartment may be provided between the interior and exterior surfaces of the balloon, as shown at 60 of FIG. 8B. Although distal inflation compartment 60 is shown with the passageway formed between the outside of the catheter shaft and the membrane forming the balloon, a distal inflation compartment may be provided which communicates with any inflation means disclosed herein.

Referring to FIG. 10, distal inflation compartment 60' may alternatively be provided as part of interior 23 of balloon 22 separated from the remainder of the balloon interior.

FIG. 11 is an alternative embodiment wherein balloon 22 and shaft 13 of catheter 12 are unitary in construction.

FIGS. 12–16 are longitudinal section views of expansion of the balloon member of the catheter of the present invention. Catheter 12 as shown at FIGS. 12–16 includes optional guide wire 40 and guide wire lumen 42. The details and mechanics of balloon inflation and specific overall catheter construction will vary according to the design of the catheter, and are known in the art per se. All of these variations are acceptable for use with the balloon catheters and stent delivery systems of the present invention.

Figure 16:
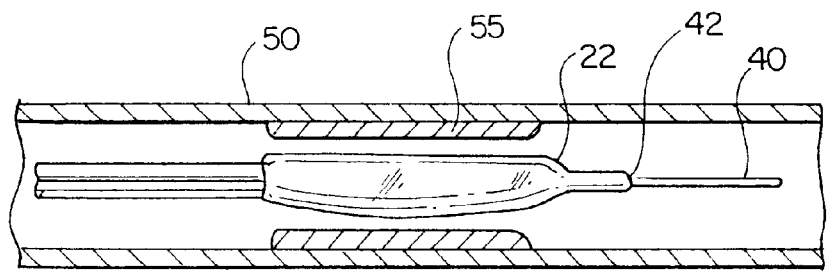

As shown in FIGS. 12 and 13, the inflation of balloon 22 is accomplished through delivery of the inflation fluid to the interior 23 of balloon 22 via distal inflation means 24 which comprises an inflation port located on the inflation lumen. At FIGS. 14–15, the inflation means is a port located at the distal end of the inflation lumen. Inflation means 24 communicates with the interior 23 of balloon 22, delivering inflation fluid to the interior 23 which inflates balloon 23 distally from the distal end to the proximal end thereof as shown at FIGS. 12 and 14. At FIGS. 12–15, balloon is shown expanding against arterial plaque 55 in vessel 50. FIG. 16 shows site 100 after deflation of balloon 22.

Figure 17:
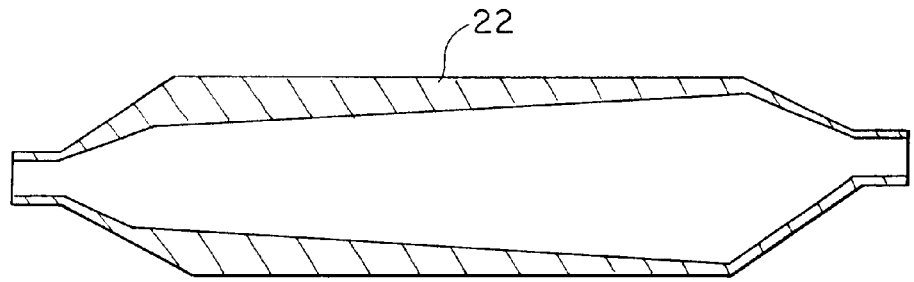
FIG. 17 is a longitudinal cross section of an alternative embodiment of a balloon according to the present invention.

Alternatively, the inflation of the balloon could be controlled by providing graduated balloon wall thickness, or through modification of the heat set temperature of the balloon material. The more compliant distal portion would expand first. An example of a balloon with graduated wall thickness is shown at FIG. 17. A balloon of a material which has a modified heat set temperature such that the balloon will inflate at its distal end first and inflate from the distal end to the proximal end thereof will appear substantially like the balloons shown in the other figures herein. The placement of the inflation means of such embodiments could be provided along any portion of the balloon, as the distal to proximal inflation is controlled in this embodiment by the balloon and balloon material itself. Any balloon inflation means known in the art including those which are proximally located with respect to the balloon may be employed in these embodiments.

The process and equipment for forming the balloon are known in the art.

Figure 18:
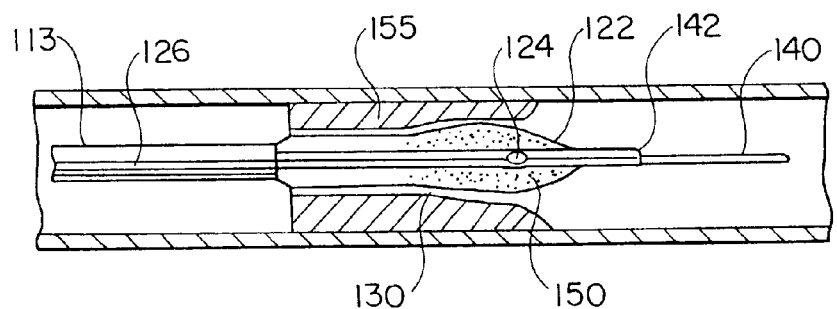
FIGS. 18–22 are longitudinal section views of delivery of a stent by a stent delivery catheter according to the present invention.
Figure 19:
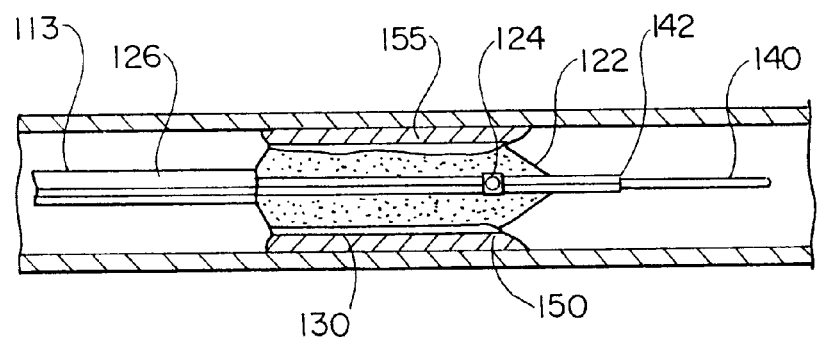
Figure 20:
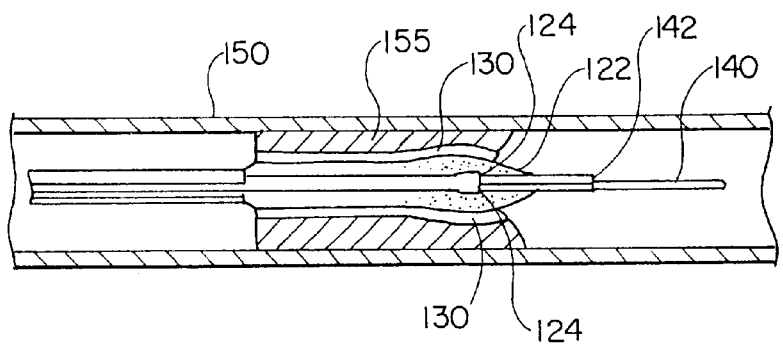
Figure 21:
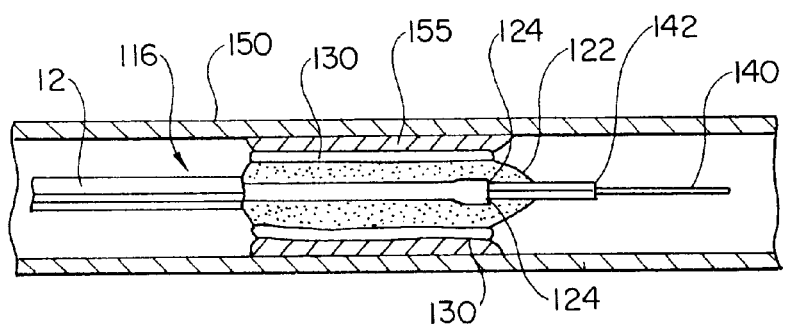
Figure 22:
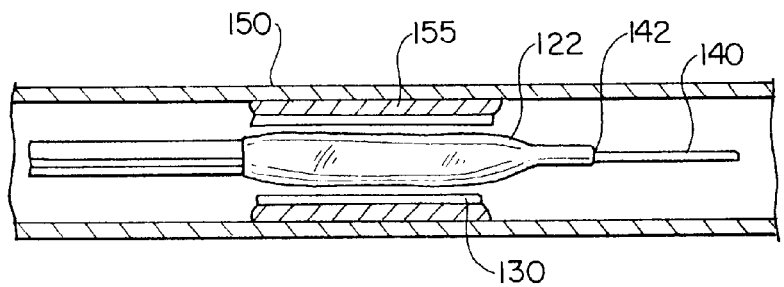

Referring to FIGS. 18–22, stent delivery catheter with a balloon member according to the present invention is shown. FIGS. 18–19 show an inflation means as in FIGS. 12–13 and FIGS. 20–21 show an inflation means as in FIGS. 14–15. Expansion of the balloon from the distal end to the proximal end results in the expansion of the stent from the distal end to the proximal end thereof. Catheter 112 is shown in FIGS. 18–22 having an optional guide wire 140 and guide wire lumen 142.

Stents which may be used with this invention include plastic and metal stents, many of which are known in the art. Some are more well known such as the stainless steel stent shown in U.S. Pat. No. 4,735,665; the wire stent shown in U.S. Pat. No. 4,950,227; another metal stent shown in European Patent Application EPO 707 837 A1 and that shown in U.S. Pat. No. 5,445,646. All of these patents are incorporated herein by reference. Also, shape memory metal stents and/or self expanding stents may be used.

Stent 130 is typically about 15 mm long, while balloon 122 is roughly the same length. These dimensions, however, are merely representative for illustrative purposes only and are not meant to be limiting.

Stent 130 has a contracted condition and an expanded condition, being sized in its contracted condition to closely surround the catheter. Stent 130 is fixed about balloon 122 by any suitable means as known in the art. For example, stent 130 may be gently crimped onto balloon 122 either by hand or with a tool such as a pliers or the like to be mounted for delivery. Further securement may be provided, such as hubs, proximal and distal socks, for example, as set forth in U.S. Pat. No. 4,950,227 to Savin, incorporated herein by reference, and the like, or other stent securement means known in the art. Where the distal portion of the outer lumen of the catheter 112 extends through the interior of balloon 122, the distal portion of the outer lumen, it provides additional surface area to facilitate stent crimping.

Stent 130 has a larger expanded diameter which is obtained when the balloon 122 is expanded. That is, stent 130 will be released from catheter 112 upon expansion of balloon 122 to be placed in a vessel. Balloon 122 and stent 130 are shown expanding against arterial plaque 155. When balloon 122 is then deflated, removal of catheter 112 may be accomplished while leaving stent 130 in place.

Catheter balloon 122 may be inflated by fluid (gas or liquid) from a distal inflation port extending from a lumen contained in the catheter shaft 113 and opening into the distal end portion of balloon 122, or by other means, such as from fluid communication from a passageway formed between the outside of the catheter shaft 113 and the membrane forming the balloon, depending on the design of the catheter. The catheter may be associated with a source of fluid (gas or liquid) external to the catheter, whereby the fluid is delivered to the balloon or expandable member by an inflation lumen located in the catheter shaft 113 and associated with the distal end portion of balloon 122. At FIG. 22, stent 130 is shown in place in implant site 100 after the balloon has been deflated.

Alternatively, the expansion of the stent could be accomplished by providing a balloon having its expansion controlled by providing a graduated balloon wall thickness as shown at FIG. 17, or through modification of the heat set temperature of the balloon material. The more compliant distal portion of the balloon would expand first, resulting in expansion of the stent from the distal end to the proximal end. The placement of the inflation means of such an embodiment could optionally be provided at any portion of the balloon, as the distal to proximal inflation is controlled in this embodiment by the balloon material itself. Any proximal balloon inflation means known in the art may be employed in this embodiment.

The details and mechanics of balloon inflation and deflation and specific overall catheter construction will vary according to the design of the catheter, and are known in the art per se. All of these variations are acceptable for use with this invention.

Important advantages are provided by the distal to proximal inflation provided according to the present invention. Distal inflation prevents the release or dislodgment of thrombus or plaque downstream. In addition, distal to proximal inflation serves to minimize vessel wall trauma resulting from stent "dumbbelling".

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A catheter balloon having a proximal end, a distal end and an interior portion, said balloon being adapted for expansion from a distal end thereof, the balloon comprising a distal expansion compartment.

2. The balloon of claim 1 further comprising an exterior wall and an interior wall, and a distal expansion compartment located between said interior and exterior walls.

3. The balloon of claim 2 further comprising an interior expansion compartment, the distal expansion compartment exterior to the interior expansion compartment.

4. A medical device comprising:
   a catheter comprising a proximal portion, a distal portion, a shaft and an expandable member located at the distal portion, said expandable member being constructed and arranged for expanding the outer diameter of said catheter from a contracted state to an expanded state, said expandable member being adapted for expansion from a distal end thereof, the expandable member having an inflation port at the distal end thereof for receiving an inflation fluid therein.

5. The medical device of claim 4 wherein the expandable member comprises a balloon, the inflation port at the distal end of the balloon the device further comprising an inflation lumen associated with a source of inflation fluid, said inflation lumen communicating with the distal portion of the balloon through said inflation port.

6. The medical device of claim 5 wherein the inflation lumen extends through the interior portion of the balloon.

7. The medical device of claim 5 wherein the inflation lumen is exterior of the balloon.

8. The medical device of claim 5 wherein the expandable member comprises a balloon made of a material which resiliently deforms under radial pressure.

9. The medical device of claim 8 wherein the balloon is made of a material selected from the group consisting of elastomeric materials, non-compliant materials, semi-compliant materials and compliant materials.

10. The medical device of claim 9 wherein the balloon is made of at least one material selected from the group consisting of polyethylene (PE), nylon, polyamide, polyether block amides (PEBAX), polyethylene terephthalate (PET), silicone, POC, polypropylene and polyether block PBT.

11. The medical device of claim 9 wherein the balloon further comprises a proximal portion and a distal portion, and said distal portion is made of a material which is relatively more compliant that the material of which the proximal portion is made.

12. The medical device of claim 10 wherein the balloon is formed of multiple layers.

13. The medical device of claim 10 wherein the balloon is coextruded.

14. The medical device of claim 5 wherein the catheter is made of a material selected from the group consisting of high density polyethylene, low density polyethylene, nylons, Pebax, Grilamid, Vestamid, Cristamid, and combinations thereof.

15. The medical device of claim 5 wherein the catheter shaft is made of a metal selected from the group consisting of stainless steel and Nitinol.

16. The medical device of claim 15 wherein the catheter shaft has an exterior lubricious coating selected from the group consisting of hydrophilic coatings and silicone coating.

17. A stent delivery system comprising:
a catheter comprising a proximal portion, a distal portion, a shaft and an expandable balloon located at the distal portion, said balloon having a proximal end and a distal end and being constructed and arranged for expanding the outer diameter of said balloon from a contracted state to an expanded state, said balloon being adapted for expansion from a distal end thereof, the balloon having an inflation port at a distal portion thereof,
an inflation lumen in fluid communication with the inflation port for supplying an inflation fluid to the balloon;
a radially expandable stent of generally cylindrical configuration positioned around said distal portion of said catheter around the balloon, said stent having a contracted condition, being sized in the contracted condition to closely surround the balloon in the contracted state, and further being expandable to an expanded condition;
expansion means associated with the balloon for expansion of the balloon from the distal end thereof first and in a proximal direction, whereby said stent is adapted for expansion from a distal end thereof to a proximal end thereof in response to the expansion of the balloon and release of the stent by expansion of the balloon.

18. The stent delivery system of claim 17 wherein the balloon is made of a material which resiliently deforms under radial pressure.

19. The stent delivery system of claim 17 wherein the stent is crimped to the balloon for delivery.

20. A catheter balloon having a proximal cone portion, a body portion adjacent to the proximal cone portion and a distal cone portion adjacent to the body portion, the catheter balloon characterized by a decreasing inner diameter and a constant outer diameter over the length of the body.

21. The balloon of claim 2 further comprising a non-distal expansion compartment, the distal and non-distal expansion compartment arranged side-by-side along the length of the balloon.

22. A catheter balloon having a proximal end, a distal end and a body portion disposed between the proximal end and the distal end, the balloon having an inflation port in the distal end through which an inflation fluid may be supplied to the balloon.

23. A medical device comprising:
a catheter comprising a proximal portion, a distal portion, a shaft and a balloon located at the distal portion, said balloon being constructed and arranged for expanding from a contracted state to an expanded state, said balloon being adapted for expansion from a distal end thereof, said balloon comprising a distal expansion compartment.

24. The medical device of claim 23 wherein said balloon further comprises an exterior wall and an interior wall, said distal expansion compartment located between said interior and exterior walls.

25. The balloon of claim 24 further comprising an interior expansion compartment, said distal expansion compartment exterior to and disposed about the interior expansion compartment.

26. The balloon of claim 24 further comprising a non-distal expansion compartment, the distal and non-distal expansion compartment arranged side-by-side along the length of the balloon.

27. A catheter balloon having a proximal cone, a body portion adjacent to the proximal cone and a distal cone adjacent to the body portion, the balloon being adapted for expansion from a distal end thereof, the balloon having an exterior wall of increasing thickness along the length of the body portion in the proximal direction.

28. The catheter balloon of claim 27 wherein the outer diameter of the body portion of the balloon in the expanded is uniform.

* * * * *